(12) United States Patent
Biswas et al.

(10) Patent No.: US 8,841,470 B1
(45) Date of Patent: Sep. 23, 2014

(54) PROCESS FOR PREPARATION OF NITROGEN-CONTAINING VEGETABLE OIL-BASED LUBRICANT ADDITIVE

(75) Inventors: Atanu Biswas, Peoria, IL (US); Kenneth M. Doll, Peoria, IL (US); Huai Nan Cheng, Metairie, LA (US); Brajendra K. Sharma, Savoy, IL (US)

(73) Assignees: The United States of America, as represented by the Secretary of Agriculture, Washington, DC (US); The Penn State Research Foundation, University Park, PA (US)

( * ) Notice: Subject to any disclaimer, the term of this patent is extended or adjusted under 35 U.S.C. 154(b) by 108 days.

(21) Appl. No.: 13/216,841

(22) Filed: Aug. 24, 2011

Related U.S. Application Data

(60) Provisional application No. 61/377,140, filed on Aug. 26, 2010.

(51) Int. Cl.
*C07C 227/00* (2006.01)
*C07C 53/00* (2006.01)
*C07C 229/00* (2006.01)
*C10L 1/222* (2006.01)

(52) U.S. Cl.
USPC .......... 554/114; 554/103; 554/220; 554/108; 554/163; 554/142; 560/19; 508/500

(58) Field of Classification Search
None
See application file for complete search history.

(56) References Cited

U.S. PATENT DOCUMENTS 2,445,892 A * 7/1948 Swern et al. ................. 554/108
3,148,199 A * 9/1964 De Groote et al. ............ 554/51
4,243,819 A * 1/1981 Henrick et al. ............... 562/433

OTHER PUBLICATIONS

Biswas, A., et al., Synthesis of an amine-oleate derivtive using an ionic liquid catalyst, Aug. 31, 2009, Journal of Agricultural and Food Chemistry, vol. 57, No. 18, pp. 8136-8141.*
Sing S., et al., Synthesis of beta-amino alcohols form methyl epoxy stearate, Feb. 22, 2010, Ind. ENg. Chem. Res., vol. 49, No. 7, pp. 3106-3111.*
Martynov, V.F., et al., Compunds containing a three-member oxide ring. XIV. Reactin of some ethyl estrs of beta-monoalkyl-substituted glyceridic acids with aniline, 1955, Zhurnal Obshchel Khimil, vol. 25, pp. 1519-1523, 2 pages abstract provided.*

(Continued)

*Primary Examiner* — Yate K Cutliff
(74) *Attorney, Agent, or Firm* — John D. Fado; Howard V. Owens

(57) ABSTRACT

Chemically-modified fatty acids are prepared by reacting epoxidized fatty acids, their esters or triglyceride oils with amines of cyclic or aromatic hydrocarbons. The fatty acid derivatives produced are of the formula:

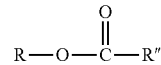

wherein R is an H, branched or straight chain alkyl or alkenyl group, aromatic-containing group, glycerol, or glyceride, R" is a C3 to C29 aliphatic chain comprising one or more of the derivatized methylene groups of the formula:

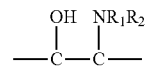

wherein $R_1$ and $R_2$ are independently selected from the group consisting of H, cyclic hydrocarbons, substituted cyclic hydrocarbons, and aryl groups, with the proviso that only one of said $R_1$ and $R_2$ may be H. These fatty acid derivatives have utility as antiwear/antifriction additives for industrial oils and automotive applications.

25 Claims, 5 Drawing Sheets

(56) References Cited

OTHER PUBLICATIONS

Pastour, P., Condensatins of acetoacetanilide with aliphatic aldehydes, 1953, Compt. Rend., vol. 237, 1094-6, 1 page abstract provided.*

Sadkh-Zade, S.I., et al., Synthesis of unsaturated esters of beta-substituted glycidic acids, 1971, Vop. Neftekhim, No. 3, pp. 149-157, 1 page abstract provided.*

Biswas, A., et al., Synthesis of diethylamine-functionalized soybean oil, 2005, J. Agric. Food Chem., vol. 53, No. 24, pp. 9485-9490.*

Mistry, B., et al., Prooxidant effects of monoglycerides and diglycerides in soybean oil., 1988, J. Food Science, vol. 53, No. 6, pp. 1896-1897.*

* cited by examiner

PROCESS FOR PREPARATION OF NITROGEN-CONTAINING VEGETABLE OIL-BASED LUBRICANT ADDITIVE

CROSS-REFERENCE TO RELATED APPLICATIONS

This application claims the benefit under 35 U.S.C. 1.19(e) of U.S. provisional 61/377,140 filed Aug. 26, 2010, the contents of which are incorporated by reference herein.

BACKGROUND OF THE INVENTION

1. The Field of the Invention

The invention relates to novel nitrogen-containing fatty ester derivatives and a process for their preparation.

2. Description of the Prior Art

Antiwear/antifriction lubricants typically comprise a base oil that has been blended with any number of additives that enhance the ability of the base oil to withstand the mechanical stresses of interacting working surfaces under boundary lubrication conditions. Most of the lubricants and many of the additives currently in daily use originate from petroleum base stocks that are toxic to environment, making it increasingly difficult for safe and easy disposal. There has been an increasing demand for "green" lubricants [Rhee, I., NLGI Spokesman, 60 (5):28 (1996)] and lubricant additives in recent years due to concerns about loss of mineral oil-based lubricants to the environment and increasingly strict government regulations controlling their use.

Vegetable oils are readily biodegradable, safe to handle, environmentally friendly, non toxic fluids that are also readily renewable resources [Salunkhe, D. K. et al., World Oil Seed Chemistry, Technology and Utilization, Van Nostrand Reinhold, New York, (1992) pp. 1-8; Bockish, M. (ed.) Fats and Oils Handbook, AOCS Press, Champaign, (1998) 838]. The triacylglycerol structure of vegetable oil, which is also amphiphilic in character, give it an excellent potential as a candidate for use as a lubricant or functional fluid [Zaher, F. A. et al., Vegetable oils and lubricants, Grasas Aceites (Seville), 39:235-238 (1988); Willing, A., Chemosphere, 43:89-98 (2001)]. Triacylglycerol molecules orient themselves with the polar end at the solid surface making a close packed monomolecular [Brockway, L. O., J. Colloid Sci., 2:277-289 (1947)] or multimolecular layer [Fuks, G. I., Research in surface forces, A. B. V. Deryagin (ed.) Consultants Bureau, New York (1963) 29-88] resulting in a surface film on the material being lubricated. In addition, the vegetable oil structure provides sites for additional functionalization, offering opportunities for improving on the existing technical properties such as thermo-oxidative, low temperature stability and lubricity. These properties make them very attractive for industrial applications that have potential for environmental contact through accidental leakage, dripping, or generation of large quantities of after-use waste materials requiring costly disposal [Randles, S. J., et al., J. Syn. Lubr., 9:145-161 (1992); Dick, R. M., Process, 41:339-365 (1994)].

Limitations on the use of vegetable oil in its natural form as an industrial base fluid or as an additive relate to poor thermal/oxidation stability [Becker, R., et al., Lubr. Sc., 8:95-117 (1996); Adhvaryu, A., et al., Thermochimica Acta, 364 (1-2): 87-97 (2000) and ref. within], poor low temperature behavior [Asadauskas, S., et al., J. Am. Oil Chem. Soc., 76: 313-316 (1999); Adhvaryu, A., et al., Thermochimica Acta, 395:191-200 (2003) and ref. within], and other tribochemical degrading processes [Brophy, J. E. et al., Ann N.Y. Academy Sci., 53:836-861 (1951); Miller, A. et al., Lubr. Eng., 13:553-556 (1957)] that occur under severe conditions of temperature, pressure, shear stress, metal surface and environment. To meet the increasing demands for stability during various tribochemical processes, the oil structure has to withstand extremes of temperature variations, shear degradation and maintain excellent boundary lubricating properties through strong physical and chemical adsorption with the metal. The film-forming properties of triacylglycerol molecules are believed to inhibit metal-to-metal contact and progression of pits and asperities on the metal surface. Strength of the protective fluid film and extent of adsorption on the metal surface dictate the efficiency of a lubricant's performance. It has also been observed that friction coefficient and wear rate are dependent on the adsorption energy of the lubricant [Kingsbury, E. P., ASLE Trans., 3:30-33 (1960)].

The antiwear properties of commercial additives are derived from a variety of elements capable of reacting with the metal surface and establish a stable protective film. Phosphorus, sulfur, nitrogen and zinc constitute the active element in most mineral oil based commercial antiwear additives. However, due to environmental and toxicological considerations, phosphorus may eventually be phased out from usage in the automotive industry because it has been implicated with catalyst deactivation fitted in catalytic converters [Wei, Dan-ping, Lubr. Sci., 7:365-377 (1995)].

SUMMARY OF THE INVENTION

By virtue of this invention, we now provide a novel class of chemically-modified fatty acids prepared by reacting epoxidized fatty acids, their esters or triglyceride oils with amines of cyclic or aromatic hydrocarbons. In the process, an epoxidized fatty acid or an ester thereof comprising one or more oxirane rings of the formula:

is reacted with an amine of the formula $R_1$—NH—$R_2$, wherein $R_1$ and $R_2$ are independently selected from the group of H, cyclic hydrocarbons, substituted cyclic hydrocarbons, and aryl groups with the proviso that only one of $R_1$ and $R_2$ may be H. In the reaction, the oxirane ring is opened and forms a nitrogen fatty acid derivative comprising one or more derivatized methylene groups of the formula:

Thus, the resultant fatty acid derivatives of this invention are of the formula:

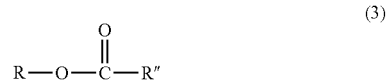

wherein R is an H, branched or straight chain alkyl or alkenyl group, aromatic-containing group, glycerol, glycerides (including O-monoglyceride or O-diglyceride), R″ is a C3 to C29 aliphatic chain comprising one or more of the above-mentioned derivatized methylene groups:

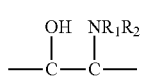
(2)

wherein $R_1$ and $R_2$ are as described above. The fatty acid derivatives so produced have utility as antiwear/antifriction additives for industrial oils and automotive applications.

In accordance with this discovery, it is an object of this invention to provide novel fatty acid and triglyceride oil derivatives.

It is also an object of the invention to provide environmentally-friendly fatty acid and triglyceride oil-based industrial fluids having acceptable antiwear/antifriction performance properties.

Another object of the invention is to introduce a new use for triglyceride oils and to expand the market for an agricultural commodity.

A further object of the invention is to produce industrial fluids that reduce the demand on petroleum resources and that are biodegradable.

It is another object of the invention to provide a synthetic route for converting epoxidized sites of unsaturation in fatty acids and triglyceride fatty acid esters to amine functionalities.

Other objects and advantages of this invention will become readily apparent from the ensuing description.

DETAILED DESCRIPTION

Figure 1:
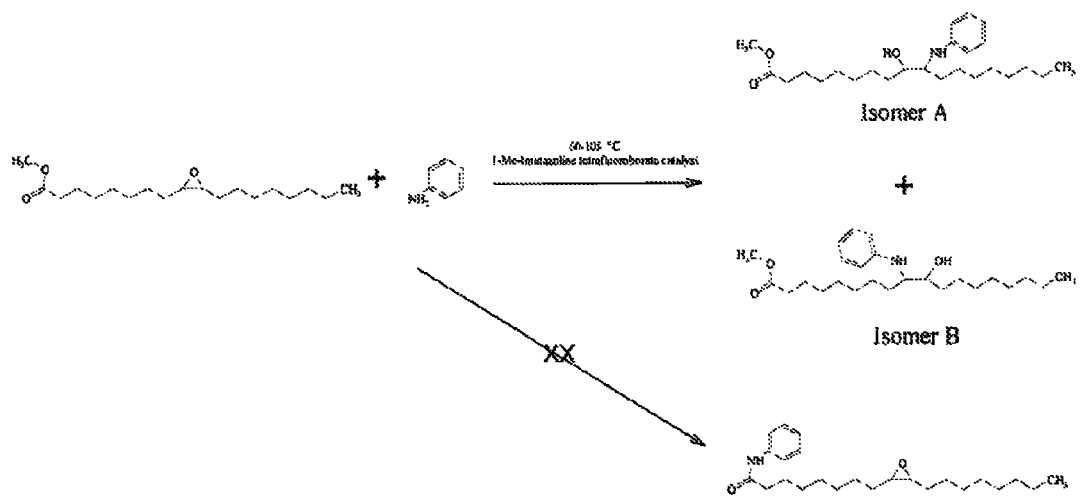
FIG. 1 shows the reaction of EMO with aniline catalyzed by 1-methyl imidazoline catalyst. Two isomers of the ring opened product were observed whereas a potential byproduct, a fatty amide, was not found.

Using the process of this invention, fatty acid ester derivatives may be formed from the epoxides of a variety of unsaturated fatty acids (with olefins), vegetable oils, animal fats, or alkyl esters of vegetable oil or animal fat. These epoxides may be produced as described below or obtained from commercial sources. When preparing the epoxides, the starting unsaturated fatty acid is not critical, and any $\Delta^3$ to $\Delta^{17}$ unsaturated fatty acid (i.e. having a double bond between $\Delta^3$ and $\Delta^{17}$ inclusive) containing from 4 to 30 carbon atoms or longer may be used. Thus, starting fatty acids include fatty acids of the formula R'—COOR wherein R' is a straight or branched chain olefin, and R is H, branched or straight chain alkyl or alkenyl groups, aromatic containing groups, or glycerides (including mono-, di- or triglycerides). Preferred starting fatty acids include, but are not limited to free and esterified, unsaturated $\Delta^3$ to $\Delta^{17}$ unsaturated fatty acid containing from 4 to 22 carbon atoms, more particularly free and esterified unsaturated $\Delta^3$ to $\Delta^{17}$ unsaturated fatty acid containing from 8 to 22 carbon atoms, and most particularly free and esterified unsaturated $\Delta^9$ to $\Delta^{15}$ unsaturated fatty acid containing from 8 to 22 carbon atoms. Examples of particularly preferred unsaturated fatty acids which may be used herein include free and esterified palmitoleic acid (16:1, $\Delta^9$), oleic acid (18:1, $\Delta^9$), linoleic acid (18:2, $\Delta^{9,12}$), erucic acid (22:1, $\Delta^{13}$), and linolenic acid (18:3, $\Delta^{9,12,15}$), 5-eicosenoic acid (20:1, $\Delta^5$), 5-docosenoioc acid (22:1, $\Delta^5$), 5,13-docosadienoic acid (22:2, $\Delta^{5,13}$), petroselinic acid (16:1, $\Delta^6$), elaidic acid (18:1, $\Delta^9$), and trans isomers of any of the above.

Unsaturated fatty acids are naturally occurring in a variety of plant oils or animal fats and may be conveniently obtained for use therefrom. Without being limited thereto, oils which may be used as sources include soybean, cottonseed, corn, olive, peanut, palm, sesame, sunflower, canola, castor, safflower, linseed, grapeseed, oiticia, tung, rice, crambe, high erucic rape, and high oleic canola oils, with soybean oil being particularly preferred.

As starting materials to prepare the epoxides, the unsaturated fatty acids may be provided in substantially pure form or, in the alternative, they may be provided as a mixture or in impure form. Moreover, although the unsaturated fatty acids may be free acids, the reaction may also be conducted using fatty acids which are esterified with aliphatic alcohols such as methanol, ethanol, isopropanol, or branched chain alcohols such as 2-ethyl hexanol or Guerbet alcohols, or with glycerol as mono-, di- or triglycerides. However, because fatty acids occur predominantly as triglycerides in triglyceride oils, the above-mentioned naturally occurring oils are preferably used directly in the reaction, thereby foregoing the need for any preliminary fatty acid synthesis and isolation of the oil.

In a preferred embodiment wherein the fatty acids are present as triglycerides, the oils principally contemplated herein include what are normally referred to as the triglyceride drying oils. The vegetable triglyceride drying oils include plant oils and plant source-like synthetic and semi-synthetic triglycerides that can be transformed into hard, resinous materials [see Encyclopedia of Polymer Science and Technology, H. F. Monk et al., eds., John Wiley & Sons, (1966), pp. 216-234]. The expression "drying oils" is generic to both true drying oils, which dry (harden) at normal atmospheric conditions, and semidrying oils, which must be baked at elevated temperatures in order to harden. Unless otherwise indicated, "drying oil" will be used herein in its broadest sense to refer to both types of drying oil. The unsaturated fatty acids (e.g., linoleic or linolenic) residues of a drying or semi-drying oil comprise double bonds that are readily available for entering into an oxidative reaction, or other reactions involved in the drying process. These oils may also include oleic fatty acid residues. Common sources of drying oils include cottonseed oil, castor oil, canola oil, linseed oil, oiticica oil, safflower oil, soybean oil, sunflower oil, corn oil, and tung oil. Of these oils, soybean oil is most readily available in both its unmodified and epoxidized state, and is therefore the most preferred. The properties of the subject industrial lubricants can be tailored by blending together different drying oils, or by blending drying oils with non-drying oils. Non-drying oils substantially comprise saturated and/or monounsaturated fatty acid residues, such as those characteristic of palmitic, stearic and oleic acid. Exemplary nondrying oils include palm, peanut, olive, and grapeseed oils.

Because of ready availability and low cost, the preferred vegetable oil use herein is soybean oil. The fatty acid constituents of soybean oil are mainly oleic (18:1), linoleic (18:2) and linolenic (18:3) acids. Though the relative distribution of fatty acids is largely dependent on the soybean type and its genetic makeup, soybean oil typically consists of approximately $C_{16}$=4%, $C_{18}$=3%, $C_{18:1}$=22%, $C_{18:2}$=66% and $C_{18:3}$=5%. The generic chemical structure of triglyceride oils for use in the invention is represented by the formula, below:

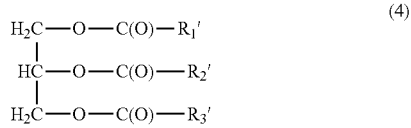
(4)

wherein $R_1'$, $R_2'$ and $R_3'$ are independently selected from C3 to C29 aliphatic fatty acid residues, that may be completely saturated or have sites of unsaturation and/or hydroxylation, provided that $R_1'$, $R_2'$ and $R_3'$ collectively have at least 1 but preferably more sites of unsaturation. In most of the common triglyceride oils listed above, the triglyceride esters are composed of C18 and C16 fatty acids, and accordingly $R_1'$, $R_2'$ and $R_3'$ are C17 or C15.

The practitioner skilled in the art will of course recognize that for fatty acid products requiring a high degree of purity or uniformity, the oils may first be hydrolyzed to obtain free fatty acids for use as starting materials in the reaction. Hydrolysis of the oils to the fatty acids may be achieved using conventional splitting techniques or alkali splitting of fats. Suitable alkali splitting techniques include, for example, treatment with sodium methoxide, or sodium or potassium hydroxide [see "A.O.C.S. Tentative Method Ca 6b-53", in: Official and Tentative Methods of the American Oil Chemist's Society, third edition, AOCS, Chicago, Ill., (1973)]. Other conventional techniques including splitting with steam under pressure are also effective.

Once the starting material has been selected, the free or esterified unsaturated fatty acids are reacted under conditions and for a period of time effective to at least partially, but preferably completely, epoxidize the carbon/carbon double bonds therein. These epoxidized fatty acids will contain one or more oxirane rings (which may also be referred to as epoxidized methylene groups):

(1)

or the equivalent formula:

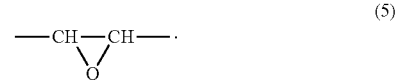
(5)

A variety of techniques for the epoxidation of olefins are known in the art and are suitable for use herein. For example, without being limited thereto, suitable techniques include those described by Qureshi et al. (Polymer Science and Technology, Vol. 17, Plenum Press, p. 250), Croco et al. (U.S. Pat. No. 5,166,372), Nowak et al. (U.S. Pat. No. 6,740,763 or 6,734,315), and preferably Bunker and Wool (Synthesis and characterization of monomers and polymers for adhesives from methyl oleate. *J. Polym. Sci., Part A: Polym. Chem.* 2002, 40, 451-458), the contents of each of which are incorporated by reference herein. In accordance with the preferred embodiment, epoxidation is effected by reaction of the unsaturated fatty acid with a combination of a peroxide and a carboxylic acid or its anhydride, or by reaction with a peroxycarboxylic acid such as peroxy-benzoic acid. Suitable peroxides include hydrogen peroxide or any organic peroxides which will form a peracid with a carboxylic acid or its anhydride. However, preferred epoxidation reagents include hydrogen peroxide with either formic acid, benzoic acid, acetic acid, or acetic anhydride. The order of addition is not critical, and the peroxide and carboxylic acid may be combined prior reacting with the fatty acid, or they may be added separately to the fatty acid, or all of the peroxide, carboxylic acid, and fatty acid may be combined concurrently. The reaction is preferably conducted at low temperatures, more preferably between about 0 and about 30° C., most preferably between about 0 and about 25° C. Because the reaction is exothermic, the temperature is preferably controlled such as by cooling. Temperature control is particularly preferred when reacting free, non-esterified fatty acids to prevent reaction of the acid moiety and polymerization. In a particularly preferred embodiment reaction is initiated at a temperature of approximately 0° C. and maintained at this temperature for about 1 hour, before the temperature is allowed to increase to room temperature. The reaction is typically completed in approximately 3 to 6 hours.

As an alternative to producing the epoxidized fatty acids or their esters, it is understood that many of these same epoxidized fatty acids and fatty acid esters (e.g., mono-, di- and triglycerides) may be obtained in pure form or as mixtures from commercial sources. In this embodiment, the epoxidation reaction is thereby unnecessary and the invention may proceed directly with the esterification reaction described herein. The final products will of course be the same.

In accordance with the process of this invention, the fatty acid epoxide produced or otherwise obtained as described above is reacted with a primary or secondary amine of a cyclic or aromatic hydrocarbon to form a fatty acid derivative wherein the oxirane ring is opened and converted to a hydroxy amine comprising a hydroxyl group at one carbon of the opened oxirane ring and an amine at the other carbon of the opened oxirane ring. A variety of amine reactants are suitable for use herein and may be represented by the formula $R_1$—NH—$R_2$, wherein at least one of $R_1$ and $R_2$ must be a cyclic or aromatic hydrocarbon or substituted cyclic or aromatic hydrocarbon. Thus, $R_1$ may be H, a cyclic hydrocarbon or substituted cyclic hydrocarbon, and $R_2$ may be a cyclic or aromatic hydrocarbon or substituted cyclic or aromatic hydrocarbon. The length of the cyclic or aromatic hydrocarbons is not critical, and may be as small as 3 carbons, with C3 to C40 hydrocarbons being preferred and C6 to C22 hydrocarbons being more preferred. The cyclic hydrocarbon may be saturated or unsaturated, substituted or unsubstituted, as well as heterocyclic, although aryl amines, wherein one or both of $R_1$ and $R_2$ are an aryl moiety are preferred. Aniline, substituted anilines, 1-naphthylamine, tolidine, procaine (2-(diethylamino)ethyl 4-aminobenzoate), phenacaine [(1E)-N, N'-bis(4-ethoxyphenyl)ethanimidamide], orthocaine(methyl 3-amino-4-hydroxybenzoate), amidol (2,4-diaminophenol), Chloramben (3-amino-2,5-dichlorobenzoic acid), 4-amino-2,6-diphenylphenol, and other aromatic amines are particularly preferred amine reactants. The reaction is optionally conducted in the presence of a effective amount of a catalyst. Suitable catalysts should be capable of opening the oxirane ring of the epoxide, and a variety of catalysts may be used, including ionic liquids, mineral acids, Lewis acids, acidic resins, and enzymes, with ionic liquids, mineral acids or Lewis acids being preferred. By way of example and without being limited thereto, suitable catalysts include $H_2SO_4$, $H_3PO_4$, $BF_3$ etherate, $CeCl_3$, $ZnCl_2$, $InCl_3$, $SBCl_2$, $AlCl_2$, $Zn(ClO_4)_2$, $Cu(ClO_4)_2$, 1-methyl imidazolium tetrafluoroborate and other ionic liquids such as 1-butyl-3-methylimidazolium chloride, 1-allyl-3-methylimidazolium chloride and choline chloride/urea, acidic resins such as AMBERLYST-15 (Rohm Haas), and enzymes such as lipases. The amount of the catalyst may vary somewhat with the particular catalyst selected, although even very small amounts are effective. Without being limited thereto, typically the catalyst will be added at a concentration of about 0.5% or higher (measured by weight of the reaction mixture), preferably at a concentration of about 1 to 10%, and most preferably at a concentration of about 5%. Although the use of a solvent is optional, the reaction is preferably conducted neat, without the addition of solvent. The reaction temperature is not critical, and the reaction is typically conducted at a temperature below about 120° C., preferably between about 60 to 105° C. Reaction time may vary with temperature and catalyst concentration, and the reaction typically reaches completion in less than about 2 hours at 105° C. with 5% catalyst by weight, and about 8-24 hours at 60° C. At the completion of the reaction, the ionic liquid catalyst may be recovered and recycled.

The reaction of the epoxidized fatty acid or its ester with amine, $R_1$—NH—$R_2$, occurs in a single step, with the oxirane ring opening and forming a secondary or tertiary amine fatty acid derivative comprising one or more derivatized methylene groups:

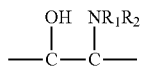

(2)

wherein $R_1$ and $R_2$ are the same as described above. Thus, if the epoxidized fatty acid or ester is represented by the formula:

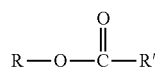

(6)

wherein R is an H, branched or straight chain alkyl or alkenyl group, aromatic containing group, glycerol, or glyceride (including O-monoglyceride or O-diglyceride), R' is a C3 to C29 aliphatic chain hydrocarbon comprising one or more of the oxirane rings, the resultant nitrogen or amine fatty acid derivative formed is:

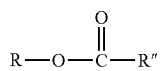

(3)

wherein R" is a C3 to C29 aliphatic chain hydrocarbon comprising one or more of the above-mentioned derivatized methylene groups. No solvent or byproducts are produced. Surprisingly, no fatty amides [i.e., R'—C(O)—$NR_1R_2$] are formed in the reaction.

When reacting fatty acid epoxides in triglyceride (formula 4 above), diglyceride or monoglyceride form, the resulting compounds may be characterized by formulas:

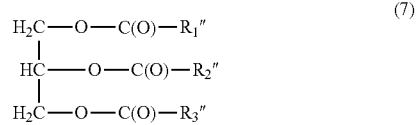

(7)

or:

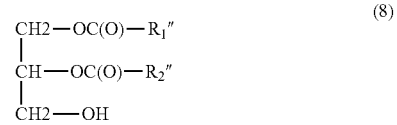

(8)

or:

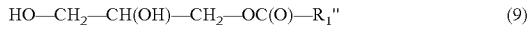

(9)

Respectively, wherein $R_1''$, $R_2''$ and $R_3''$ are independently selected from C3 to C29 aliphatic fatty acid residues comprising one or more of the hydroxy amine derivatized methylene groups:

(2)

wherein $R_1$ and $R_2$ are the same as described above.

The nitrogen or amine fatty acid derivatives of this invention have superior properties which render them useful as additives to base stocks for biodegradable lubricant applications, such as crankcase oils, transmission fluids, two-cycle engine oils, marine engine oils, greases, hydraulic fluids, drilling fluids, metal cutting oils, and the like. Base stocks useful in the lubricant formulations contemplated by the invention are typically high molecular weight hydrocarbons, and may be of mineral, vegetable, or synthetic origin, or mixtures thereof. Exemplary base oils are described in Erickson et al. (U.S. Pat. No. 5,023,312, the contents of which are incorporated herein by reference). Of course, the objectives of the invention to maximize the biodegradability of the lubricant system would be achieved with a vegetable oil base stock.

Though formulations of base stocks with the nitrogen or amine fatty acid derivatives of the invention meet or exceed many, if not all, specifications for lubricant end-use applications, it is contemplated that other additives may be used in conjunction with the nitrogen or amine fatty acid derivatives in order to enhance the properties of the base stock. Illustrative of these additives are detergents, antiwear agents, antioxidants, viscosity index adjusters, pour point depressants, corrosion protectors, friction coefficient modifiers, colorants and the like as well-known in the art.

The amount of nitrogen or amine fatty acid derivative additive formulated with a base oil will of course depend upon the end-use application of the formulation. For most of the end-uses indicated above, the concentration of additive will be in the range of about 1-12% (w/w), typically at least about 4% (w/w), and preferably in the range of about 5-8% (w/w).

The following examples are intended only to further illustrate the invention and are not intended to limit the scope of the invention as defined by the claims.

Example 1

The reaction, between epoxidized methyl oleate and aniline to produce an oleate-aniline adduct, without the formation of fatty amide, is described. This reaction was carried out neat, with a catalytic amount of an ionic liquid as described in Biswas et al. [J. Agricultural and Food Chemistry, 57:8136-8141 (2009)], the contents of which are incorporated by reference herein.

Experimental

Materials

Methyl oleate (Tech 70%), hydrogen peroxide (A.C.S. Reagent, 30% Solution), formic acid (96%, A.C.S. reagent), hexanes (>95%, HPLC grade), Aniline (99.5% reagent grade) from Sigma-Aldrich, St. Louis, Mo.; Methyl oleate (>99%) from Nu check Prep, Elsyian, Minn.; 1-Methylimidazole (99%) from Acros; Tetrafluoroboric acid 48% min w/w aq. solution from Alfa Aesar; NaCl (A.C.S. Reagent), NaHCO$_3$ (A.C.S. Reagent) from Fisher, Fairlawn, N.J., were all used as received.

Epoxidized methyl oleate(methyl 9,10-epoxy stearate; EMO) has been previously used in our laboratory in order to make a variety of different oloechemicals [Doll et al., Ind. Eng. Chem. Res., 46:3513 (2007); Doll and Erhan, J. Agric. Food Chem., 53:9608 (2005); and Doll and Erhan, Green Chem., 2008, 10:712 (2008)]. The same synthesis was used here, which was adapted from Wool et al. [La Scala and Wool, J. Amer. Oil Chem. Soc., 79:373 (2002)] and originally based on Swern epoxidation [Findley et al., J. Am. Chem. Soc., 67:412 (1945); and Schmits and Wallace, J. Amer. Oil Chem. Soc., 31:363 (1954)].

Instrumentation:

GC-MS was performed on an Agilent (Santa Clara, Calif.) 7890A gas chromatograph equipped with a 7683B series injector and a 5975 C mass detector. The instrument programs and data acquisition were handled by a Windows XP equipped HP-Compaq DC7700 computer with a 3.39 GHz Pentium D processor using Agilent MSD Enhanced Chemstation Version E01.00.237. The GC column was 30 m×0.25 mm in dimensions with film thickness 0.25 um HP-5MS (Agilent, Santa Clara, Calif.). A helium flow rate of ~0.3 mL min$^{-1}$, an injection volume of 0.1 uL and a 50:1 split ratio were used. The temperatures were as follows: Inlet 220° C., Detector 220° C., Auxiliary transfer line 250° C., MSD 150° C. The initial temperature of 150° C. was held for 2 min and then ramped to 280° C. at 15° C. min$^{-1}$ where it was held for 20 min. The detector was ran in the EI mode and set to scan for m/z ratios from 50 to 500 Daltons.

NMR was performed on a Bruker (Boston, Mass.) Avance 500 NMR spectrometer operating at 500 MHz for $^1$H and 125 MHz for $^{13}$C. Bruker Icon NMR software was used on a HP x1100 Pentium 4 workstation. Peaks were referenced to sodium 3-trimethylsilylpropionate-2,2,3,3-d$_4$ (TSP) at 0.0000 ppm. Simulations of $^{13}$C NMR spectra were performed by ACD/Labs 6.00 ACD/CNMR predictor software, running on a Gateway Pentium 4 CPU with a 2.53 GHz processor.

Reactions:

1-methyl imidazolium tetrafluoroborate [Zhu et al., Green Chem., 5:38 (2003)] was prepared by taking 1-Methylimidazole (61.5 g, 0.75 mol) in a three necked flask with a stirrer and cooled to 0° C. Then tetrafluoroboric acid (0.75 mol, 40% solution in water) was added slowly over a period of 30 min while stirring and cooling to maintain the temperature at 0-5° C. The reaction mixture was stirred for an additional period of 2 h. Water was removed in vacuum to give the product as a colorless liquid, which solidified on cooling.

Aniline, 0.93 g (10 mmol) was added to an 8-gram (30 ml) glass vial containing 1.56 g (5 mmol) of epoxy methyl oleate and 0.0125 g of the ionic liquid, 1-methyl imidazolium tetrafluoroborate [Zhu et al., ibid]. The mixture was stirred with a U-shaped stirring bar at room temperature for 5 minutes. It was allowed to stand for another 5 minutes so that the layers were separated before taking the zero time aliquot from the top layer. The mixture was covered with a septum and placed in a Reacti-therm reactor set at 105° C. Samples were withdrawn after 1, 2, 4, 6, 8, 24 and 48 hours.

After withdrawing the final sample, the remaining mixture was transferred to a 125 ml separatory funnel with 30 ml of ethyl acetate, which was washed three times with 50 ml of water. The water layer was discarded, the water wash was repeated twice, and a wash with saturated solution of sodium chloride was performed. The ethyl acetate layer was transferred to a 100 ml beaker; excess sodium sulfate was added and then filtered. The filtrate was collected in a round bottom flask, from which ethyl acetate was evaporated under vacuum using a rotary evaporator. The flask was placed in a vacuum oven at 50° C. overnight. When larger amounts of ionic liquid were used, the water washes were collected and combined in a round bottom flask. Water was evaporated under vacuum using a rotary evaporator. The ionic liquid recovered in the flask was kept in a vacuum oven at 50° C. overnight to evaporate the residual water.

Oxidative Stability:

Oxidation stability evaluations of the oleate-aniline product of the reaction were done using pressurized differential scanning calorimetry. Samples of ~1.5-2.0 mg were placed in a hermetically sealed type aluminum pan with a pinhole lid for interaction of the sample with the reactant, dry air, which was pressurized in the module at a constant pressure of 1378.95 KPa (200 PSI). A scanning rate of 10° C./min was used throughout the experiment. The controlled diffusion of the gas through the hole greatly restricts the volatilization of the oil while still allowing for saturation of the liquid phase with air.

Results and Discussion

In the reaction sequence, we first start with methyl oleate and epoxidize it to form the epoxidized methyl oleate (EMO). Epoxidation is a standard procedure and can be done readily via hydrogen peroxide and formic acid catalyst. The EMO is then reacted with aniline in the presence of an ionic liquid, 1-methyl imidazolium tetrafluoroborate (FIG. 1). We discovered that whereas the ionic liquid is essential for the reaction, only a catalytic amount is needed, perhaps as low as 0.5% by weight of the reaction mixture.

The reaction is very facile. The reactants are added together, without solvents and heated to 60-100° C. for several hours. A time study has been conducted under various reaction conditions, and progress monitored by taking reaction aliquots, which are analyzed by GC-MS. (It is important to do the washing procedure to samples, as any residual catalyst will cause damage to the GC column.) The product has been fully characterized by $^1$H and $^{13}$C NMR and GC/MS.

Structural Characterization

The $^1$H and $^{13}$C NMR spectra of the reaction products are relatively complex with many peaks. This is because we have two regio-isomers present, corresponding to the attack of aniline on either position 9 or position 10 of the epoxide. (FIG. 1).

Despite the large number of distinctive carbons and proton present, we are able to achieve almost complete assignments through a combination of empirical shift rules [Cheng and Bennett, Anal. Chim. Acta, 242:43 (1991)], chemical shifts of analogous compounds [Gunstone, J. Amer. Oil Chem. Soc., 70:1139 (1993); Cheng, RAPRA Review Reports, 11 (2001); and Biswas et al., Green Chem., 9:85 (2007)], and two-dimensional NMR.

In the $^1$H NMR, the assignment of the aniline moiety is straightforward from coupling patterns and intensities: ortho, para, and meta in decreasing shielding. Protons at 9 and 10 positions can also be easily assigned because the methine attached to oxygen is more downfield than the methine attached to nitrogen. As for the other protons, we have the benefit of having the assignments of methyl oleate-aza-dicarboxylate ester [Gunstone, ibid; Cheng, (2001) ibid]. The use of the 2D HSQC data then completes the assignments. Note that protons at position 11 in product A (and position 8 in product B) show up as doublets due to asymmetry at position 10 in product A (and position 9 in product B) as a result of aniline addition.

In the $^{13}$C NMR, the assignments reasonably follow the empirical shift rules (Cheng and Bennett, (1991) ibid]. It is of interest that at 125 MHz, the two products A and B gives distinctly different peaks for all carbons, except for C-18, and carbons from aniline, methoxy and ester. Because the pairs of peaks are often very closely located, it is not always possible to positively differentiate the A and B products in each pair. Some reversal in assignments may be likely. It is of interest that Product A is slightly more preponderant than Product B. If this assumption is wrong, then some of the assignments need to be reversed.

Note also that in the $^{13}$C spectra, there is only the ester peak at 174 ppm. No fatty amide peak is observed. The positions of aniline ring carbons at 147.6 ppm (carbon attached to N), 113.5 ppm (ortho carbons), 117.2 ppm (para carbon), and 129.6 ppm (meta carbons) also confirm this observation. If the fatty amide had formed, these ring carbons would have appeared at 138.4 ppm (carbon attached to N), 121.6 ppm (ortho carbons), 124.4 ppm (para carbon), and 129.0 ppm (meta carbons). Similarly the methoxy group is also intact (at 51.4 ppm), consistent with FIG. 1.

Figure 3:
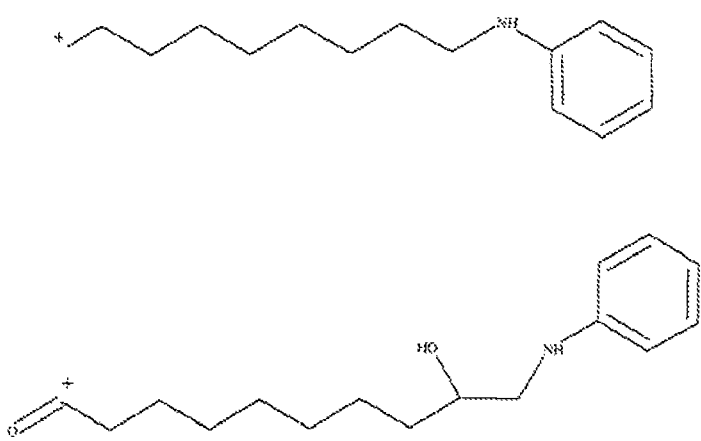
FIG. 3 shows two potential structures which correspond to the observed molecular weights in the EI MS of the products. The molecular formulas of $C_{15}N_{24}N$ and $C_{16}H_{24}O_2N$ have monoisotopic masses of 218.19 and 262.18, which correspond to the observed m/z peak in the spectra.

Additional evidence that the assigned product is correct has been shown by the MS detector on the GC. Although the molecular ion is not seen, as is expected for EI, the two largest peaks have m/z of 218.3 Da and 262.3 Da. These fragments can be assigned to the structures (FIG. 3) of probable fragments of the proposed products which have monoisotopic masses of 218.19 Da and 262.18 Da respectively.

The study on the effects of different variables on the rate of production of products provided several interesting trends. These trends demonstrate the importance of temperature, catalyst concentration, and the molar ratio of EMO:aniline on this reaction.

Effect of Temperature

This novel reaction displays strong temperature dependence. The reactions were all conducted using 2.5 g of catalyst and a 2:1 EMO:aniline molar ratio. It is clear that the reaction rate increases at higher temperatures. At 2 hours, the reaction ran at 90° C. had nearly twice the amount of products (90%) as that obtained at 60° C. (53%). Because the reaction conducted at 105° C. was complete in less than 2 hours, reaction aliquots had to be taken more frequently in order to monitor the progress of the reaction. We have used this temperature in subsequent studies of catalyst and reactant ratio experiments.

Effect of Catalyst Concentration:

We observed the effect of catalyst concentration by monitoring the initial 2-3 hours of a series of reactions, conducted at 105° C. at a 2:1 EMO:aniline molar ratio, with different amounts of added catalyst. As expected, there is no product observed in the reaction without the catalyst. However, even 0.0125 g of catalyst (0.5% by weight of reaction mixture) is enough to cause considerable product formation. At an amount of catalyst 0.125 g (5% by weight) or greater, the reaction nears completion in only 1 hour.

Effect of EMO:Aniline Ratio

A final series of experiments, with differing molar ratios of EMO:aniline was performed at 105° C. with a 2.5 g catalyst loading. First, we obtained the obvious result where no product was formed without aniline. At 1 equivalent of aniline, the products did form, but at a fairly slow rate. Nonetheless, the reaction achieved completion in 6 hours. With 2 equivalents of aniline, the reaction proceeded much faster, achieving near completion in an hour. Further excess of aniline had little additional effect.

Figure 2:
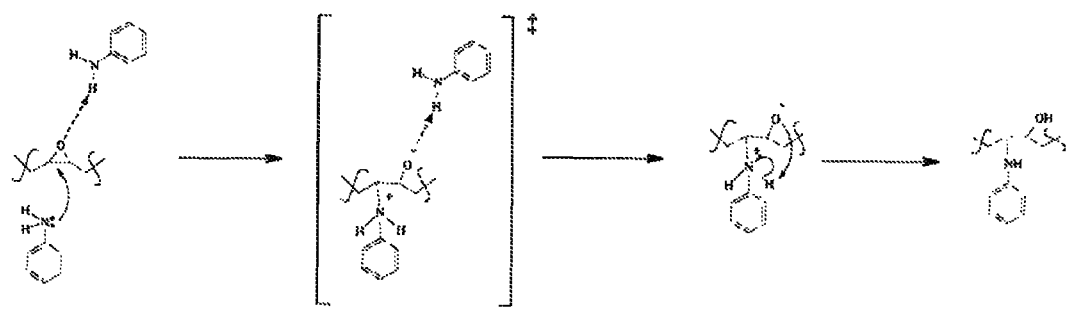
FIG. 2 shows the possible mechanism for ring opening reaction of epoxy methyl oleate with aniline.

This observation suggests that perhaps aniline serves two functions. The first molecule of aniline attacks the epoxide, and the second aniline molecule complexes with the oxygen and facilitates the ring-opening process (FIG. 2). A possible transition state is also noted in the scheme. Although a mechanism where only one aniline molecule is used has not been definitively ruled out, in either case, aniline is able to stabilize the transition state via delocalization of the cationic charge to the benzene ring. This is a potential hypothesis to explain why this reaction is more facile for an aromatic amine. Aniline may also facilitate the proton transfer from the cationic moiety to the anionic moiety. In this mechanism the role of the catalyst could be either to facilitate the initial aniline attack on the substrate or to stabilizes the transition state catalyzing the reaction, or a combination of both.

In the experiment where no aniline was used, we also monitored the loss of starting material, EMO. From this trial, it seems that initially the catalyst alone did not cause significant decomposition of the EMO, but after a long induction period, EMO loss became rapid. However, the product of this reaction was not observed by GC-MS and the reaction was not studied further.

Figure 4:
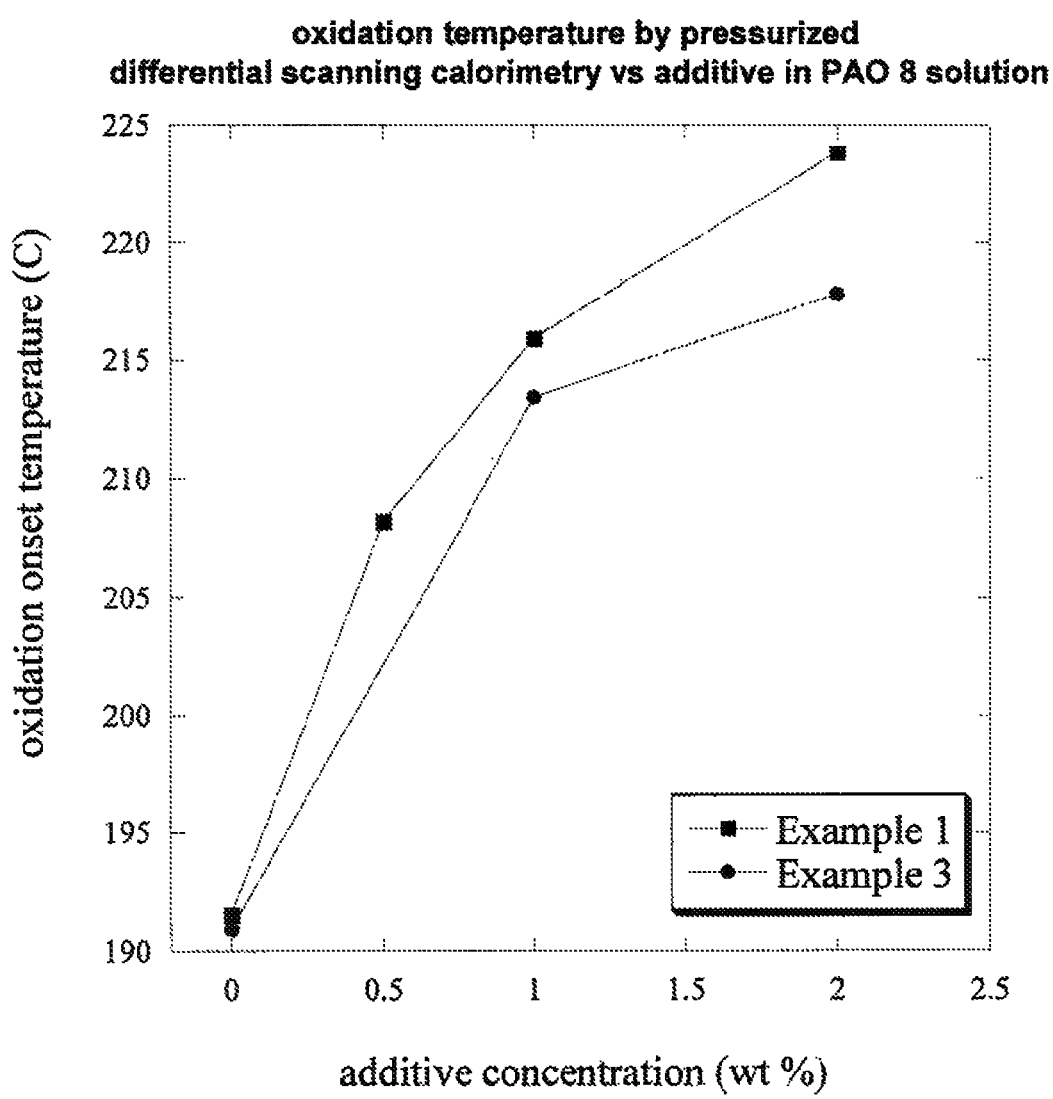
FIG. 4 shows the onset temperatures of the oxidations for PAO 8 alone and with the additive as described in Examples 1 and 3.

Oxidative Stability:

The onset temperatures of the oxidations are reported for PAO 8 alone, and with the oleate-aniline adduct as an additive (FIG. 4). The results show that the additive was able to increase the onset temperature by more than 32° C.

Conclusion

In this work, we report a facile and environmentally friendly reaction involving epoxidized methyl oleate and aniline. The advantages of this reaction are that it is easily performed, gives good yield, and requires only a small amount of ionic liquid. Furthermore, the ionic liquid can be recovered and recycled. Thus, this reaction is "green", and cost-effective.

Example 2

Lubricity Testing

Figure 5:
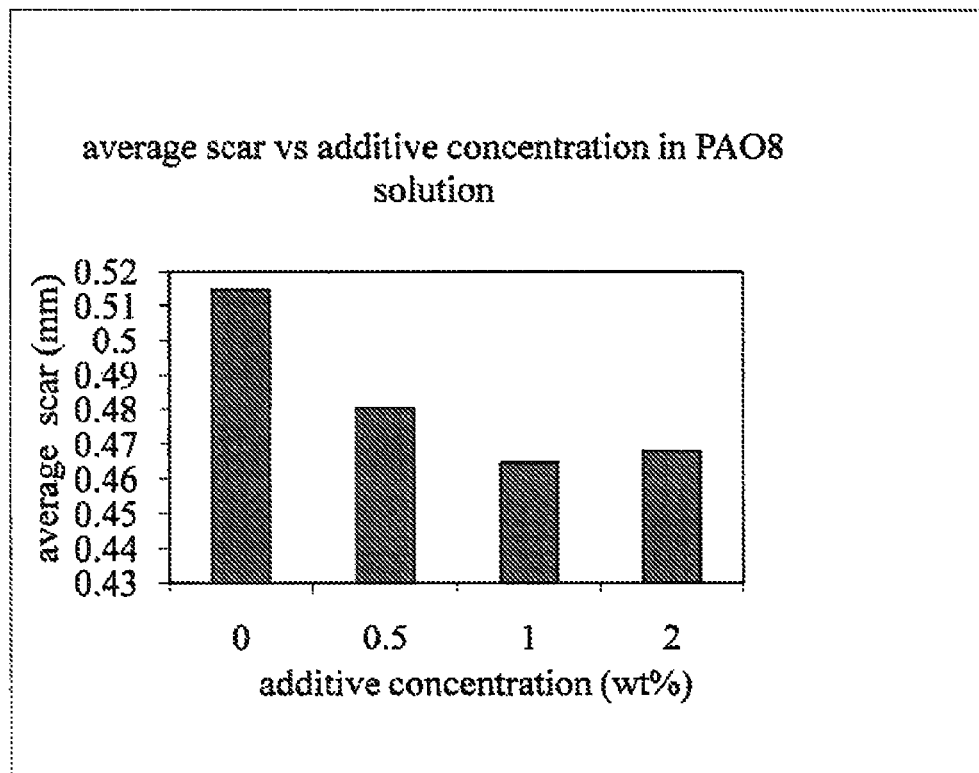
FIG. 5 shows the results of a wear scar test using polyalphaolefin and the improvement observed by adding this product at levels up to 2%.

The anti-wear properties of a sample synthesized in the manner described in Example 1 under the following conditions, (1:2 EMO:Aniline, 2.5 g IL, 48 hrs/105°) and 18233-94-9 (1:2 EMO:Aniline, 1.24 g IL, 48 hr/105°) were examined under sliding contact by four-ball test using a Falex apparatus (Model Multi-Specimen, FALEX Corporation, Sugar Grove, Ill.). The balls (52100 steel, 12.7 mm diameter, 64-66 Rc hardness and extreme polish) were thoroughly cleaned with dichloromethane and hexane before each experiment. Test samples, 7 ml of 0.5%, 1%, and 2% samples in base oil (polyalphaolefin (PAO8)), were poured in the test cup to cover the stationary balls. For the experiments, a set rpm of 1200 and a normal load of 20 kg was applied at 75° C. for 60 minutes. The wear scar diameter (WSD) on the balls was measured using a digital optical microscope. Two measurements, perpendicular to each other, were recorded for each scar on a ball and the average of six measurements, for three balls, was taken in each case. The scar diameter is reported in millimeters. Duplicate tests were always done with new set of balls. A decrease in the average scar diameter of the PAO8 solutions containing the material was observed (FIG. 5).

Example 3

This reaction was done between epoxidized soybean oil and 4-amino-2,6-diphenylphenol in the presence of an ionic liquid. The reaction was carried out using a similar procedure as in Example 1. The $^1$H NMR spectrum gives the expected peaks for epoxidized soybean oil, except that the epoxide peaks at around 3.0 ppm are diminished in intensities. The phenyl peaks are clearly visible as complex multiplets at ca. 7.3 ppm. In addition, there are small peaks at 3.5-4.2 ppm, due to the formation of aminohydrin (hydroxy amine). The NMR data indicate that the phenyl derivative is partly grafted onto soybean oil via addition to the epoxide.

This product was also tested as an additive by pressurized differential scanning calorimetry (DSC) by the same method as in example 1. In this case (FIG. 4) the results show that the additive was able to increase the onset temperature by almost −28° C.

It is understood that the foregoing detailed description is given merely by way of illustration and that modifications and variations may be made therein without departing from the spirit and scope of the invention.

We claim:

1. A method of making a derivative of a nitrogen-containing fatty acid comprising reacting (a) an epoxidized fatty acid ester of the formula:

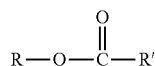

wherein R is a branched or straight chain alkyl or alkenyl group, aromatic containing group, glycerol, or glyceride, and R' is a C3 to C29 aliphatic chain comprising one or more oxirane rings of the formula:

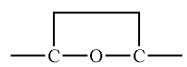

between the C2 and C16 carbon atoms thereof,
with (b) an aryl amine of the formula $R_1$—NH—$R_2$, to open said oxirane ring and form a nitrogen-containing derivative of said fatty acid ester of the formula:

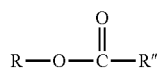

wherein said R" is a C3 to C29 aliphatic chain comprising one or more derivatized methylene groups of the formula:

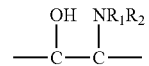

between the C2 and C16 carbon atoms thereof, wherein said $R_1$ and $R_2$ are independently selected from the group consisting of H and aryl groups, with the proviso that only one of said $R_1$ and $R_2$ may be H, and further wherein said reacting of an epoxidized fatty acid ester with said amine is conducted in the presence of an ionic liquid catalyst effective for opening said oxirane ring.

2. The method of claim 1 wherein said R' and R" are a C7 to C21 aliphatic chain.

3. The method of claim 1 wherein said R' and R" are a C16 to C18 aliphatic chain.

4. The method of claim 1 wherein said amine of the formula $R_1$—NH—$R_2$ is selected from the group consisting of aniline, substituted aniline, 1-naphthyl amine, tolidine, procaine, phenacaine, orthocaine, amidol, Chloramben, and 4-amino-2,6-diphenylphenol.

5. The method of claim 1 wherein said epoxidized fatty acid ester is selected from the group consisting of a triglyceride, diglyceride, monoglyceride, alkyl ester of triglyceride, and mixtures thereof.

6. The method of claim 5 wherein said epoxidized fatty acid ester comprises an epoxidized triglyceride.

7. The method of claim 1 wherein said epoxidized fatty acid ester comprises epoxidized triglyceride oil.

8. The method of claim 7 wherein said triglyceride oil is selected from the group consisting of soybean, cottonseed, corn, olive, peanut, palm, sesame, sunflower, canola, castor, safflower, linseed, grapeseed, oiticia, tung, rice, crambe, and rape.

9. The method of claim 1 wherein said catalyst is selected from the group consisting of 1-methyl imidazolium tetrafluoroborate, 1-butyl-3-methylimidazolium chloride, and 1-allyl-3-methylimidazolium chloride.

10. The method of claim 1 wherein said reacting of an epoxidized fatty acid ester with said amine is conducted substantially in the absence of an added solvent.

11. The method of claim 1 further comprising producing said epoxidized fatty acid ester by reacting an unsaturated fatty acid ester having one or more sites of unsaturation —C=C—, with an epoxidation reagent to form said epoxidized fatty acid wherein at least one of said sites of unsaturation of said fatty acid ester is converted to said oxirane ring.

12. The method of claim 11 wherein said unsaturated fatty acid ester comprises an ester of an unsaturated fatty acid which is selected from the group consisting of oleic acid, linoleic acid, linolenic acid, palmitoleic acid, erucic acid, 5-eicosenoic acid, 5-docosenoic acid, 5,13-docosadienoic acid, and petroselinic acid.

13. The method of claim 11 wherein said unsaturated fatty acid comprises oleic acid.

14. A compound of the formula:

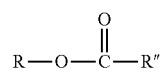

wherein said R is a branched or straight chain alkyl or alkenyl group, aromatic-containing group, glycerol, or glyceride, said R" is a C3 to C29 aliphatic chain comprising one or more derivatized methylene groups of the formula:

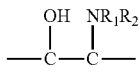

between the C2 and C16 carbon atoms thereof, wherein said $R_1$ and $R_2$ are independently selected from the group consisting of H and aryl groups, with the proviso that only one of said $R_1$ and $R_2$ may be H.

15. The compound of claim 14 wherein said R" is a C7 to C21 aliphatic chain.

16. The compound of claim 14 wherein said R" is a C16 to C18 aliphatic chain.

17. The compound of claim 14 wherein said $NR_1R_2$ is selected from the group consisting of aniline, substituted aniline, 1-naphthyl amine, tolidine, procaine, phenacaine, orthocaine, amidol, Chloramben, and 4-amino-2,6-diphenylphenol.

18. The compound of claim 14 wherein said R is selected from the group consisting of a diglyceride, alkyl esters of a diglyceride, monoglyceride, alkyl esters of a monoglyceride, and mixtures thereof.

19. The compound of claim 18 wherein said R is a diglyceride or alkyl ester of a diglyceride.

20. A composition comprising a base stock material of mineral, vegetable, animal or synthetic origin, or mixtures thereof, and a component of the formula:

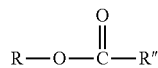

wherein said R is a branched or straight chain alkyl or alkenyl group, aromatic containing group, glycerol, or glyceride, said R" is a C3 to C29 aliphatic chain comprising one or more derivatized methylene groups of the formula:

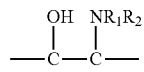

between the C2 and C16 carbon atoms thereof, wherein said $R_1$ and $R_2$ are independently selected from the group consisting of H and aryl groups, with the proviso that only one of said $R_1$ and $R_2$ may be H.

21. The composition of claim 20 wherein said R" is a C7 to C21 aliphatic chain.

22. The composition of claim 20 wherein said R" is a C16 to C18 aliphatic chain.

23. The composition of claim 20 wherein said $NR_1R_2$ is selected from the group consisting of aniline, substituted aniline, 1-naphthyl amine, tolidine, procaine, phenacaine, orthocaine, amidol, Chloramben, and 4-amino-2,6-diphenylphenol.

24. The composition of claim 20 wherein said R is selected from the group consisting of a diglyceride, alkyl esters of a diglyceride, monoglyceride, alkyl esters of a monoglyceride, and mixtures thereof.

25. The composition of claim 24 wherein said R is a diglyceride or alkyl ester of a diglyceride.

\* \* \* \* \*